United States Patent [19]

Grundfest

[11] Patent Number: 5,163,933

[45] Date of Patent: Nov. 17, 1992

[54] PROSTHETIC JOINT REPLACEMENT PROCEDURE USING EXCIMER LASER

[75] Inventor: Warren S. Grundfest, Los Angeles, Calif.

[73] Assignee: Cedars-Sinai Medical Center, Los Angeles, Calif.

[21] Appl. No.: 601,410

[22] Filed: Oct. 22, 1990

[51] Int. Cl.$^5$ ............................................. A61N 5/06
[52] U.S. Cl. ...................................... 606/99; 606/3; 623/16
[58] Field of Search .................. 606/2, 3, 82, 99; 128/395, 397, 398, 897–899; 623/16

[56] References Cited

U.S. PATENT DOCUMENTS

| | | | |
|---|---|---|---|
| 3,769,963 | 11/1973 | Goldman et al. | 128/395 |
| 3,858,577 | 1/1975 | Bass et al. | 128/398 |
| 4,207,874 | 6/1980 | Choy | 606/7 |
| 4,248,232 | 2/1981 | Engelbrecht et al. | 128/305 |
| 4,313,431 | 2/1982 | Frank | 606/15 |
| 4,316,467 | 2/1982 | Muckerheide | 606/10 |
| 4,461,283 | 7/1982 | Doi | 606/15 |
| 4,469,098 | 9/1984 | Davi | 128/395 |
| 4,641,912 | 2/1987 | Goldenberg et al. | 606/7 |
| 4,686,979 | 8/1987 | Gruen et al. | 606/7 |
| 4,702,236 | 10/1987 | Tarabichy et al. | 128/92 V |
| 4,732,448 | 3/1988 | Goldenberg et al. | 606/7 |
| 4,784,135 | 11/1988 | Blum et al. | 128/395 |
| 4,843,112 | 6/1989 | Gerhart et al. | 623/16 |
| 4,846,161 | 7/1989 | Roger | 606/99 |
| 4,868,237 | 9/1989 | Hoff et al. | 524/407 |
| 4,873,969 | 10/1989 | Huebsch | 128/92 R |
| 4,881,536 | 11/1989 | Noble et al. | 606/94 |
| 5,027,792 | 7/1991 | Meyer | 128/6 |

FOREIGN PATENT DOCUMENTS

8502532  6/1985  PCT Int'l Appl. .................... 606/7

OTHER PUBLICATIONS

"Kinetics of the Ablative Photodecomposition of Organic Polymers in the Far Ultraviolet (193nm)"by Srinivasan, vol. B1, J. Vac. Sci. Technol. (1983) pp. 923–926.

Choy et al., "Transluminal Catheter Angioplasty," American J. Cardiology, vol. 50, pp. 1206–1208 (Dec. 1982).

Forrester et al., "Lazer Angioplasty and Cardiovascular Disease" (1986).

Ronn, "Laser Chemistry," Scientific American, vol. 240, No. 5, p. 114 (May 1979).

Trokel et al., "Excimer Laser Surgery of Cornea," American J. of Opthamology, vol. 96, No. 6 (Dec. 1983).

Grundfest et al., "Comparison of Tissue Effects of Pulsed Ultraviolet Lasers To Continuous Wave YAG and Argon Lasers," (Jan. 1985).

Pellin et al., "Endoexcimer Laser Intraocular Ablative Photodecomposition" Letters to the Journal, American Journal of Opthamology (Apr. 1985).

Taylor et al., "Reinforcement of Bone Cement Using Metal Meshes," Proc. Instn. Mech. Engrs., vol. 203, p. 49, Part H: Journal of Engineering In Medicine (1989).

Primary Examiner—David M. Shay
Attorney, Agent, or Firm—Lyon & Lyon

[57] ABSTRACT

What is disclosed is a method of removing bone cement by use of an excimer laser. This method is useful in prosthetic joint replacement surgery. Ablation of the bone cement by means of the excimer laser allows for prosthetic replacement without tearing or damage to the natural tissue, bone or limb to which the prosthesis is attached. Lasers used have an intensity level of at least 50 kilowatts and wavelengths ranging from 157–400 nm.

3 Claims, No Drawings

PROSTHETIC JOINT REPLACEMENT PROCEDURE USING EXCIMER LASER

FIELD OF THE INVENTION

This invention relates to the removal, by means of an excimer laser, of bone cement for purposes of a prosthetic revision. Ablation of the cement by means of an excimer laser allows for prosthesis replacement without tearing or damage to the natural tissue, bone or limb to which the prosthesis is attached. When the cement is exposed to the laser, the chemical bonds in the cement break, releasing the prosthesis from the natural limb without the need for cutting or damage to the bone, tissue or portion of the natural limb to which the prosthesis is attached.

BACKGROUND OF THE INVENTION AND DESCRIPTION OF THE PRIOR ART

Primarily because they tend to loosen with age, certain prostheses require revision or replacement after a number of years. In order to revise or replace a prosthesis, the existing prosthesis must be removed. Depending on their position and manner of affixation, prostheses will require different methods of removal from adjacent bone or tissue. In the case of substitute joints, the prosthetic implant is cemented to the adjacent bone by the use of fitted profile pieces fastened with bone cement. The cement adheres to roughness and protrusions in the respective bone and prosthesis. The cement bond is very strong and is designed to withstand normal, and sometimes more strenuous than normal, human activity. The cement bond is so indestructible that, when a joint prosthesis is to be removed, it is sometimes necessary to cut away at the bone to which the prosthesis is cemented. It is preferable to remove as little bone as possible in order to preserve a strong foundation for the new prosthesis. The present invention overcomes the problems in removal of joint prostheses in that it removes bone cement by vaporizing it, leaving the adjacent bone and prosthesis unscathed.

Bone cement is also often used as an element of osteosyntheses—a combination of plates, nails, wires, screws and bone cement. Osteosyntheses are used for bone reconstructions such as in the case of bone fractures or to replace parts of the cranium. The present invention can be applied to remove osteosyntheses by vaporizing the bone cement.

In other applications, such as with an artificial limb, the prosthesis is anchored in the intramedullary canal of the cavity of the adjoining bone by an endoprosthesis surrounded by bone cement. The surgeon prepares the bone cavity for receiving the prosthesis and mixes the bone cement. The cement, normally initially of a doughy consistency, is then directed into the prepared bone cavity with sufficient pressure to force the cement into the interstices of the bone and to avoid air bubbles so as to provide a strong physical interlock by the bone cement after curing. The prothesis is then put in place by inserting the endoprosthesis into the cement-filled cavity. The endoprosthesis is commonly precoated with a polymer which has a tacky surface or is otherwise pretreated in order to ensure its rigid adherence to the bone cement upon curing. Removal and replacement of this type of prosthesis, therefore, requires unanchoring the endoprosthesis by removal of the bone cement. Commonly the cavities in which the prostheses are anchored are only a few millimeters in width. Often it is necessary to fenestrate the bone in order to reach the cement.

Present methods for removing bone cement include the use of impact chisels and drills in various combinations. Such techniques give unsatisfactory results. Bone cement generally has a hard, smooth surface which is difficult to grip with a chisel or drill. An impact chisel or drill consequently can tend to drift or slip during use, resulting in penetration and damage to the bone interior wall or other tissues. Considerable damage can be done to the bone by the chisel, which normally operates at 120 volts. Where the chisel or drill is used in close proximity to the spinal cord, jarring or slippage could result in death to the patient. Use of a chisel or drill also is very tedious and careful work and requires a great deal of surgical time. Time is a critical factor in surgical procedures. The stress from prolonged anesthesia is damaging to the patient, and particularly so in arthroplasty since patients tend to be old. During long surgical procedures a great loss of blood from the marrow cavity is inevitable. Loss of blood gives rise to transfusion problems and presents coagulation and other postoperative risks.

Another suggested method of bone cement removal is by the use of thermal chisel. Such a method is described in U.S. Pat. No. 4,702,236, Tarabichy et al. Thermal chisels are instruments having working bits of various shapes which are heated to a temperature exceeding the melting point of the bone cement. The chisel is then inserted into the cement, and, as the cement melts, the chisel scoops out the melted cement by the mechanism of the chisel device. The chisel penetrates the cement until arrested by the bone wall of the cavity. Repeated use of the chisel succeeds in removing substantially all of the cement. In order to operate efficiently, these chisels are heated to 400°–450° C., which temperatures are far in excess of those which can permanently damage the bone and surrounding tissue. Such problems with thermal chisels are described in U.S. Pat. No. 4,873,969, Huebsch. Since the arrestation of the thermal chisel is by making contact with the bone wall, there is a great proclivity for damage to the bone wall by use of these tools.

Yet another suggested technique for bone cement removal is described in U.S. Pat. No. 4,873,969, Huebsch. Huebsch suggests using a type of thermal chisel which is electric, but operates at less than 24 volts, and which, instead of scooping out melted cement, gently melts the cement into a sectional pattern. Later, after the cement rehardens, the sections, weakened in their new state, are removed by means of an impact chisel. This method is dissatisfactory in that it still involves the use of heat, which can damage the bone. This method does not obviate the need for impact chisels and their associated problems.

U.S. Pat No. 4,248,232, Engelbrecht et al., describes the use of an ultrasonic vibration device to loosen the bonds between bone cement and its connective component. This type of device is similar in effect to the thermal devices described above, in that the vibrations cause the cement to heat and melt, with the same resultant dangers of thermal transfer. Like Huebsch, Engelbrecht et al. require the removal of the melted or reformed cement by means of a conventional chisel tool. U.S. Pat. No. 4,868,237, Hoff et al., similarly teaches the removal of bone cement by acoustic waves including shock waves and ultrasound waves. In this method, acoustic perturbation elements (such as threads, fabrics, foils or plates) are mixed into the cement. When it comes time to remove the cemented prosthesis, the acoustic waves are directed to the cement, which causes the perturbation elements to excite and loosen the bond. This method involves problems in achieving uniform distribution of the perturbation elements and still requires the removal of the loosened cement from the bone cavity or other cemented portion of the body.

The present invention avoids the problems encountered in the prior art since it involves the use of an excimer laser. The use of an excimer laser eliminates the possibility of heat damage, and provides for more complete cement removal. Since the cement is ablated, there is no waste product to transfer out of the cavity. The present invention also takes less time than techniques known in the prior art and thus avoids the problems inherent in long surgical procedures.

Bone cements are normally based on acrylate and are prepared by mixing and polymerizing pulverulent prepolymers with liquid monomers containing initiators and accelerators for the polymerization. A widely used bone cement is poly(methyl methacrylate) (PMMA). Biodegradable bone cements such as those polyester composites described in U.S. Pat. No. 4,843,112, Gerhart et al., are also known. These latter cements are gradually absorbed by the surrounding bone and replaced with living bone tissue.

The use of lasers in medical surgery has been known since the introduction of the laser in 1960. Lasers are now commonly used in ophthalmologic surgery to treat detached retinas, or to remove corneal tissue. Thermal energy laser application, such as photocoagulation, is used in correcting detached retinas. The radiant energy of the laser is converted into thermal energy in the tissue, denaturing the organic proteins therein, and thereby producing a lesion of denatured protein. The resulting lesion provides a base upon which the detached retina adheres, thus correcting the detachment. Another form of thermal laser application, thermal destruction, is used to remove tumors and skin lesions; however this method suffers from thermal complications such as carbonization or charring of concentric areas of surrounding tissue. See, e.g., Choy et al., "Transluminal Catheter Angioplasty," *American J. Cardiology*, vol. 50, pp 1206–08 (December 1982).

Laser photodecomposition, which utilizes non-thermal pulsed radiation of specified energy, wavelength, frequency and pulse duration from an excimer laser, is preferable in procedures in which the thermal effects of burning or denaturation is to be avoided, such as in the case of removing prostheses from limbs, where it is desirable not to cause damage to the bone or tissue surrounding the bone cement. See, e.g., Srinivasan et al., *American Journal of Ophthalmology*, vol. 96, p. 710 (1983) and its discussion of removing target tissue without damage to surrounding corneal tissue. The present invention employs such photodecomposition techniques.

There are two postulates as to the operation of ablative photodecomposition. The first, photochemical desorption, involves the electronic excitation of the constituent bonds of the material to be removed, followed by bond breaking and the production of volatile fragments which evaporate or escape from the surface of the material. The second postulate is that the excimer laser, as a result of its short pulse duration capability, has the capacity to vaporize the undesired material at such a rapid rate that the rate of destruction exceeds the ability of that material to conduct the heat away to surrounding tissue. The heating is so rapid that it is only superficial, and the vaporization carries away the heat before it has time to penetrate below the surface by conduction. See, e.g., Forrester et al., Laser Angioplasty and Cardiovascular Disease (1986); Ronn, "Laser Chemistry," *Scientific American*, vol. 240, No. 5, p. 114 (May 1979).

Ablative photodecomposition has been used on polymers such as synthetic plastics, cartilage and human hair. See, Trokel et al., "Excimer Laser Surgery of Cornea," *American Journal of Ophthalmology*, vol. 96, No. 6 (December 1983). Perhaps because of their microlesioning effects and tissue-penetrating characteristics, excimer lasers have proved to be particularly useful in surgical procedures in the eye, central cervix and gastrointestinal tract. Their effectiveness in cutting skin and muscle and removing plaque has been evaluated. Lasers have been used to remove tissue, atherosclerotic plaque, kidney stones, knee ligaments, vascular obstructions and calcified tissue—all biological organic tissues and matter. However, in terms of the removal of synthetic, non-naturally occurring matter the laser has not been used extensively.

Background information regarding lasers and the use of lasers in medical applications can be found in U.S. Pat. No. 3,769,963 which describes an instrument for performing laser microsurgery. The specification provides a great deal of background information regarding lasers and laser applications for a variety of medical purposes, and we incorporate the information disclosed therein by reference. Methods of using FAR ultraviolet radiation of to produce an ablative photodecomposition to remove biological tissue and avoiding pyrolysis as the dominant mechanism for removal of the biological matter so as to minimize incidental heat damage is described in WO 85/02532 and U.S. Pat. No. 4,784,135. U.S. Pat. No. 4,316,467 describes a method for treating skin defects and lesions in which a system for regulating the laser energy output in accordance with the absorption of the tissue being irradiated is used. The method described by these patents is limited to the removal of biological matter. The removal of synthetic materials such as bone cement is yet unexplored.

The present invention presents a new application for excimer lasers, and a new and superior method of bone cement removal than known before in the art. The present invention employs photodecomposition techniques in a novel manner and for purposes wholly undiscovered heretofore by the medical community.

In medical application, lasers are often used with fiberoptics devices as a means of reaching internally located points of interest in the human body, without the need for invasive openings made in the body. Such fiberoptic devices can be used in connection with the present invention in order to reach within bone cavities or other internally positioned cement portions. A fiberoptic device is comprised of a plurality of usually clad plastic or glass tubes wherein the cladding is of a lower index than the core for each tube. The outstanding feature of fiberoptics devices is the ability to bend light around corners. In many medical applications, the fiberoptic devices have been combined with laser techniques in order to properly focus and apply the laser energy to interior parts of the body. Thus use of laser and fiberoptic art and combinations thereof in surgery are not new generally. Specific uses include those described in U.S.

Pat. Nos. 3,858,577; 4,316,467; 4,313,431; 4,461,283; 4,469,098; and 4,207,874. These patents disclose entirely different applications than the present invention when the purposes, subject matter and methods of application are compared.

The present invention embodies the functions necessary to safely and efficiently remove a synthetic prosthesis which has been securely cemented to natural tissue or bone of the human body. Several considerations are addressed by the invention. Access must be gained to the bone cement, and the laser moved to close proximity therewith. The portion of the cement to be removed must be precisely located and illuminated to guide the operation. The laser device must be flexible enough to avoid damage to the tissue or prosthesis. The glue must be removed so as not to produce obstruction or build-up.

A primary object of the invention is to combine the laser and fiberoptic techniques in an application which enables the necessary location of, observation of, ablation and separation of prosthesis and tissue, without damage to prosthesis or surrounding tissue.

BEST MODE FOR CARRYING OUT THE INVENTION

Whereas the invention has a multitude of useful applications, the following will describe one such application, namely, the removal of bone cement from the intramedullary canal of the cavity of the thigh bone, into which a lower leg endoprosthesis has been anchored.

An excimer laser such as that described in WO 85/02532 is used, the laser apparatus having a power source, a sealed metallic housing having top, bottom and side plates made of non-conductive metal, and a sealed, gas-tight laser excitation chamber for dispersion of the laser gas mixture. The excitation chamber contains a laser gas medium which upon excitation produces an excimer (excited dimer). Preferred lasing gas media include one from the noble gases Ar, Kr, Ne and Xe and a second species from the halogens Fl, Cl, Br and I.

At opposite ends of the laser body are mirrors aligned with a window and an electrical discharge zone. One mirror is totally reflective for complete reflection of laser radiation. The other mirror is only partially reflective allowing for the transmission of laser output energy through the mirrored surface for ultimate delivery to the bone cement site.

In operation, the excited laser gas medium emits radiation through the partially transmissive mirror into a fused silica fiberoptic waveguide which is attached to the laser body in alignment with the laser discharge zone. The radiation is conveyed via the fiberoptic waveguide to the site where the bone cement is to be removed. To make the fiberoptic accessible to the bone cement in the intramedullary canal, the fiberoptic wavelength is directed through an endoscopic means such as an arthroscope which extends from a point outside the body through the patient's leg, through the outer bone wall and into the intramedullary canal where the bone cement resides.

The laser radiation discharged vaporizes the bone cement. The preferred embodiment employs a laser having a wavelength range of 157–400 nm and an intensity level of at least 50 kilowatts. Such lasers are commercially available. The radiation is applied in short pulses of about 10 nsec in duration. The laser is applied to all remaining portions of the bone cement until all traces have been eliminated, or until enough bone cement has been eliminated to allow removal of the prosthesis under optimum conditions.

These apparatus and methods of treatment have been described in order to make the invention known to those skilled in the art; the foregoing description should be taken as illustrative and not limiting in any sense.

I claim:

1. A method removing bone cement, comprising the steps of:
   providing an excimer laser device;
   providing an arthroscope;
   inserting the arthroscope into a human body;
   moving the arthroscope to a position in the human body where bone cement is located; and
   directing laser radiation from the excimer laser through the arthroscope to the bone cement in a pulsed output of approximately 10 nanoseconds duration and at an intensity level of at least 50 kilowatts;
   wherein the laser radiation so directed photoablates the bone cement without causing damage to surrounding bone or tissue.

2. The method of claim 1 wherein the step of providing an arthroscope provides a flexible arthroscope.

3. The method of claim 2 wherein the steps of inserting the arthroscope into a human body and moving the arthroscope to a position in the human body where bone cement is located includes inserting the flexible arthroscope in the human body to a position adjacent the bone cement.

* * * * *